(12) United States Patent
Busse et al.

(10) Patent No.: US 6,669,366 B2
(45) Date of Patent: Dec. 30, 2003

(54) X-RAY DETECTOR PROVIDED WITH INTEGRATED COOLING

(75) Inventors: Falko Busse, Aachen (DE); Heinz Van der Broeck, Zuelpich (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 116 days.

(21) Appl. No.: 09/994,361

(22) Filed: Nov. 26, 2001

(65) Prior Publication Data

US 2002/0071523 A1 Jun. 13, 2002

(30) Foreign Application Priority Data

Nov. 27, 2000 (DE) ......................... 100 58 818

(51) Int. Cl.[7] ............................... H01J 35/10
(52) U.S. Cl. ...................................... 378/199
(58) Field of Search ................. 378/127, 130, 378/199, 200, 141; 250/310, 352, 370.15, 397

(56) References Cited

U.S. PATENT DOCUMENTS

| 4,831,639 A | * | 5/1989 | Harke .................... 378/19 |
| 5,811,816 A | * | 9/1998 | Gallagher et al. ..... 250/370.15 |
| 6,511,224 B1 | * | 1/2003 | Lu et al. .................. 378/199 |

FOREIGN PATENT DOCUMENTS

| DE | 29510802 | 10/1995 | ............ A61B/6/02 |
| EP | 0182040 A1 | 5/1986 | ............ A61B/6/03 |
| EP | 0182040 | 11/1988 | ............ A61B/6/03 |

* cited by examiner

Primary Examiner—William Oen
(74) Attorney, Agent, or Firm—John Vodopia

(57) ABSTRACT

The invention relates to an X-ray examination apparatus in which the X-ray detector 1 and the X-ray source 2 are subject to keeping the temperature constant and to cooling by way of a common cooling circuit. To this end, a cooling medium of constant temperature is applied to the X-ray detector 1 in order to make the X-ray detector 1 operate at uniform ambient temperatures. The temperature of the cooling medium, thus increased a first time, still suffices to perform cooling of the X-ray source 2. Consequently, the heated cooling medium, after application to the X-ray detector 1, is applied to the X-ray source 2 where a second exchange of heat takes place, so that at the same time the X-ray source 2 is cooled without utilizing an additional cooling circuit. This offers the advantage that relevant X-ray examination apparatus may have a simple construction, that the electronic components used in the construction have a correspondingly prolonged service life due to the constant low temperature, and that the apparatus can operate with a higher mean power as a result of the cooling.

9 Claims, 2 Drawing Sheets

X-RAY DETECTOR PROVIDED WITH INTEGRATED COOLING

FIELD OF THE INVENTION

The invention relates to an X-ray examination apparatus which includes an X-ray detector and an X-ray source which are arranged on a supporting device. The invention also relates to an X-ray detector which includes a sensor unit that converts X-rays into electrical image signals and in which a sensor unit is adjoined by a processing unit that includes a plurality of amplifier units. The invention also relates to a method for cooling X-ray examination apparatus.

BACKGROUND OF THE INVENTION

The X-rays emitted by an X-ray source in imaging X-ray examination apparatus traverse a patient or object to be examined and are attenuated in conformity with the different thickness and chemical composition of the tissue or the bones to be examined. In the X-ray detector the X-rays are converted into light in a scintillating material or into charge carriers that can be detected directly.

X-ray examination apparatus are used, for example in the field of surgery and consist, for example, of a mobile console and a mobile supporting device which is attached thereto and accommodates on the one side an X-ray source and on the opposite side an image pick-up device or the X-ray detector.

With a view to achieving easy mobility, the weight of the entire system is compensated. To this end, balancing weights are provided in given locations. The power fed into the X-ray source is converted substantially completely into heat which is dissipated mainly via the housing of the X-ray source. Because the permissible ambient temperature of the X-ray apparatus may not exceed a given value, the mean power must be limited and the housing must have a sufficiently large surface area. However, the latter can be realized to a limited extent only because of the weight and the room that is required, for example for the surgery.

The image pick-up devices or X-ray detectors being used thus far and consisting of an X-ray image intensifier and a camera will be replaced in future by flat dynamic X-ray detectors. This development is described, for example in EP 440282. Such systems realize a considerable saving of weight that is of enormous importance to the mobility. However, in order to make this saving of weight effective for the entire system, a corresponding reduction of weight must also be realized for the X-ray source. The latter, however, is possible to a limited extent only. Inter alia the necessary dissipation of heat prevents an adequate reduction of weight to be achieved for the same amount of X-rays. The problems are worsened by the fact that a flat X-ray detector makes it possible to realize higher mean continuous powers.

EP 0182040 discloses a cooling device for a computed tomography apparatus. Because of their structural configuration, computed tomography apparatus produces a very large amount of heat which must be limited on the one hand to prevent influencing of the patient to be examined who is arranged within the ring and on the other hand to prolong the service life of the computer tomography apparatus, notably of the X-ray tube. Therefore, the X-ray source is cooled by means of a cooling medium. Because the X-ray source and the X-ray detector are mounted on a ring, the X-ray source is cooled by means of a system of ducts that is situated in the ring and contains oil. The oil that is heated by the dissipation of heat from the X-ray source is applied to the ring via a cooling medium outlet opening and is transported around the ring by a circulation pump so as to reach the X-ray source again via the cooling medium inlet opening. The path through the ring is used to cool the heated cooling medium. The cooling oil can also be cooled by channels in the ring that contain air. The cooling ducts are arranged in the stationary part of the ring. Cooling ribs that are provided on the mobile part of the ring project into the cooling ducts in the stationary part of the ring and are cooled therein, thus enabling cooling of the cooling oil present in the system of ducts. The present invention proposes direct cooling of the X-ray source.

DE 29510802 U1 describes a surgical X-ray diagnostic device in which the X-ray generator and the X-ray image intensifier are mounted on a C arm. Cooling of the X-ray generator is possible via a double-walled construction of the C arm.

SUMMARY OF THE INVENTION

It is an object of the invention to provide a device in which the temperature in the X-ray detector can be kept constant and at the same time the overall weight of the overall X-ray examination apparatus can be kept small.

This object is achieved in accordance with the invention in that there is provided an X-ray examination apparatus which includes a supporting device, an X-ray detector and an X-ray source and a system of ducts which is coupled to a heat exchanger, is associated with the X-ray detector and the X-ray source and is intended to receive a cooling medium.

The invention is based on the idea that the operation of an X-ray detector is very stable and that it generates similar image signals when all of its components are subject to the same temperature. Assuming that the temperature in such an X-ray detector is not very high, a cooling medium that is used to keep the temperature constant will not be severely heated. The X-ray source produces considerably more heat than the X-ray detector. Therefore, the cooling medium that can be readily heated and is used first of all for keeping the temperature in the X-ray detector constant is used additionally for cooling the X-ray source. An additional cooling device for the X-ray source can thus be dispensed with, so that the complexity of an X-ray examination apparatus is considerably reduced and hence also its overall weight.

The cooling medium in a preferred embodiment of the device is applied to the X-ray detector via a first sub-duct system with a constant temperature.

It is thus achieved that the components in the X-ray detector operate under the same temperature conditions, so that uniformly amplified image signals are produced. Moreover, the internal temperature of the X-ray detector is kept low, so that the sensor unit for converting the X-rays into electrical signals that is situated within the X-ray detector operates in the range of highest sensitivity. The cooling medium takes up a first amount of heat in the X-ray detector; however, this amount is not very large so that the cooling medium is applied, without further cooling, to the X-ray source via a second sub-duct system for further cooling. After the cooling of the X-ray source, the heated cooling medium is applied to a heat exchanger in which it is cooled to the initial temperature.

The X-ray detector in a preferred embodiment of the invention is provided with temperature sensors which apply a temperature-dependent signal to the heat exchanger so as to enable temperature control. The heat exchanger is preferably arranged outside the supporting device; however, a compact heat exchanger can also be integrated in the C arm or be arranged on the C arm when the construction of the overall system is to be smaller.

From the heat exchanger the cooling medium, preferably water, is first applied to the detector at a low but constant temperature of, for example 20° C., in which it realizes the necessary temperature stabilization. The cooling liquid that has been slightly heated therein, for example to 25° C., is then transported to the housing of the X-ray source in which it takes up further heat. The X-ray source is accommodated in a housing and consists essentially of the X-ray tube. The high voltage transformer with rectifier may optionally be accommodated in the same housing; in that case it is not necessary to realize the power supply with a high voltage. The console accommodates the power supply and the control circuitry. After the cooling of the X-ray source, the cooling liquid is applied with a higher temperature to the heat exchanger in which it is cooled to a lower temperature again. The liquid may be routed via the supporting device or the C arm. The heat exchanger may have such a simple construction that it provides only the constant low temperature for the detector. Any dissipation of heat in the housing of the X-ray source reduces the direct heat output and hence enables a novel construction of the X-ray examination apparatus with a lower weight or with a higher mean continuous power of the X-ray examination apparatus.

This device makes it possible to ensure that the X-ray source does not exceed a maximum temperature and that the X-ray detector operates at a constant temperature.

The object of the invention is also achieved by means of an X-ray detector that is provided with a sensor unit which converts the X-rays into electrical signals and is adjoined by a processing unit which includes a plurality of amplifier units. The plurality of amplifier units is associated with the cooling unit in such a manner that the temperature of all amplifier units can be kept constant while the scintillator unit present in the sensor unit is cooled at the same time.

Dynamic X-ray detectors are used in the field of medical diagnostics. They are considered to be universal detector components that can be used in various application-specific X-ray apparatus. An important property thereof is the possibility of acquisition of X-ray images and X-ray image sequences with low X-ray doses. To this end, an as high as possible signal-to-noise ratio of the X-ray detector is pursued. In order to enable stable operation of the flat dynamic X-ray detectors, therefore, it is necessary to keep the temperature in the X-ray detector constant. In order to ensure this with an appropriate degree of effectiveness and reliability, external cooling is proposed in accordance with the invention.

Flat dynamic X-ray detectors have a layer-like construction. The sensor unit includes a scintillator unit for converting the incident X-rays into visible light. The scintillator unit is associated with a photosensitive reading unit which may be implemented by photodiodes or phototransistors. The charge carriers read out are applied to a processing unit in which the electrical signals read out are amplified. The sensor unit is subdivided into a multitude of image points which are arranged in the form of a matrix. The charge carriers generated are read out in rows or columns and applied to a plurality of amplifier units that are associated with corresponding image zones. In order to achieve uniform amplification in uniform conditions, it is necessary that all of said amplifier units operate in the same temperature range. To this end, the amplifier units are associated with a cooling unit in accordance with the invention. The cooling unit receives a cooling medium which enables the temperature of all amplifier units to be kept constant. To this end, the cooling unit is supplied with a cooling medium that has a constant, low temperature, for example from a heat exchanger as mentioned above. The temperature of all amplifier units present in the X-ray detector is thus adjusted to a uniform value, so that they all amplify the image signals under the same temperature conditions.

A further advantage of this arrangement resides in the fact that the arrangement of a cooling unit in such an X-ray detector can keep the internal temperature of the X-ray detector low so that the sensitivity of the scintillator unit can be adjusted accordingly. It is a characteristic of the scintillator unit that the sensitivity in converting X-rays into electrical charges decreases as the temperature increases.

An X-ray detector in a further embodiment in accordance with the invention is provided with a cooling device in accordance with the invention and performs a direct conversion of charge carriers into electrical signals.

A further advantage offered by the arrangement in accordance with the invention resides in the fact that because the temperature of the X-ray detector as well as especially of the individual amplifier units is kept low, the service life of the electronic components required for operation is prolonged.

The object is also achieved by means of a method for cooling X-ray examination apparatus in which a cooling medium is applied to an X-ray detector and the heated cooling medium is applied, after a first exchange of heat between the cooling medium and the X-ray detector, to the X-ray source for the purpose of cooling.

BRIEF DESCRIPTION OF THE DRAWINGS

An embodiment of the invention will be described in detail hereinafter with reference to the drawings. Therein.

DETAILED DESCRIPTION OF THE PREFERRED EMBODIMENTS

Figure 1:
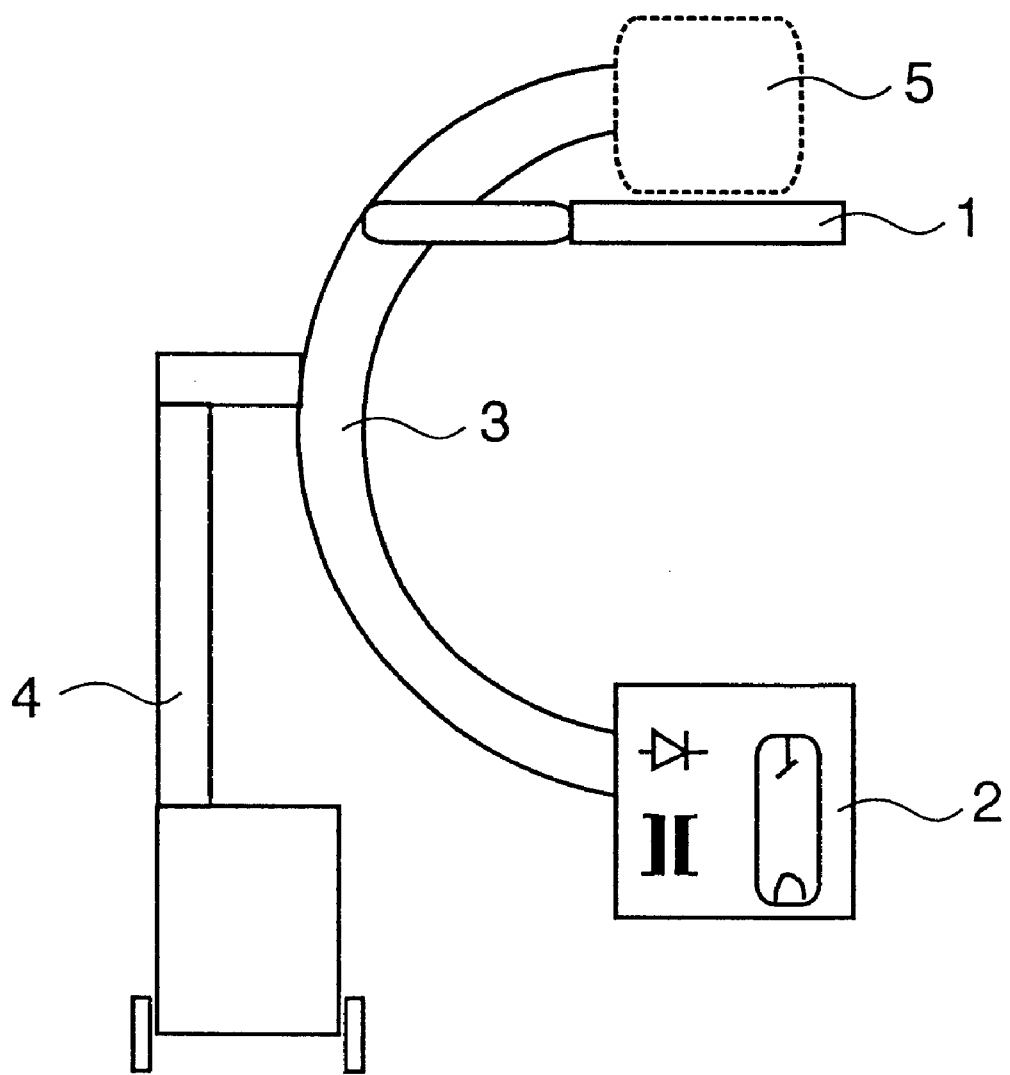
FIG. 1 shows an X-ray examination apparatus.

FIG. 1 shows an X-ray examination apparatus which is constructed as a C arm X-ray examination apparatus. The flat dynamic X-ray detector 1 and the X-ray source 2 are both mounted on the supporting device 3 which is connected to the console 4. The supporting device 3 of the present embodiment is constructed as a C arm. As is represented by the unit 5, the flat dynamic X-ray detector 1 may also be replaced by a conventional image intensifier.

Figure 2:
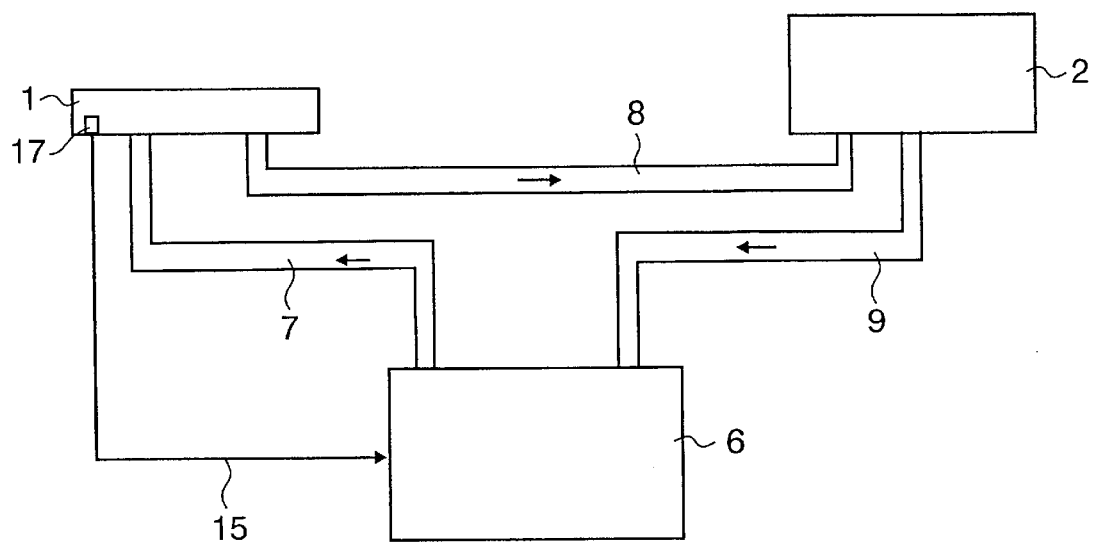
FIG. 2 shows a cooling circuit with an X-ray detector and an X-ray source.

FIG. 2 shows the cooling circuit between the heat exchanger 6, the dynamic X-ray detector 1 and the X-ray source 2. The cooling medium in the form of water or oil of a constant temperature of 20° C. is fed, via a first sub-system 7 of the duct system, to the X-ray detector 1. Therein, a first exchange of heat takes place between the X-ray detector 1 and the cooling medium. The cooling medium, now having a temperature of 25° C., is applied to the X-ray source 2 via a second duct sub-system 8. The X-ray source produces temperatures in excess of 50° C. The supply of the cooling medium to the X-ray source enables a second exchange of heat which reduces the temperature of the X-ray source to a maximum of 50° C. The second exchange of heat heats the cooling medium to, for example 35° C. The cooling medium that has thus been heated again is applied, via the third duct sub-system 9, to the heat exchanger 6 in which the cooling medium is cooled to the temperature of 20° C. again. One or more temperature sensors 17 are provided in the X-ray detector in order to generate a signal 15 that is dependent on the temperature in the X-ray detector and is applied, via the lead 15, to the heat exchanger 6 for the purpose of temperature control.

Figure 3:
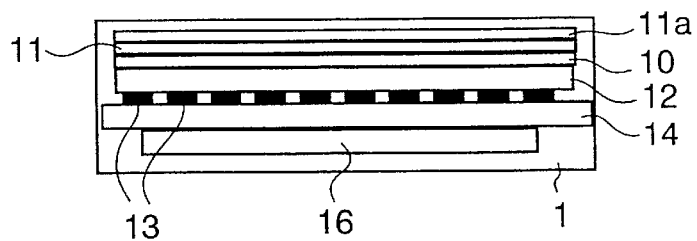
FIG. 3 is a detailed representation of a dynamic X-ray detector.

FIG. 3 is a detailed representation of a dynamic X-ray detector 1. The X-ray detector 1 consists of an X-ray converter unit 1 la, a sensor layer 11 and a glass layer 10 that is provided underneath the sensor unit 11. Underneath the sensor unit 11 there is provided a processing unit 12 which includes a plurality of amplifier units 13. The amplifier units 13 serve to amplify the image signals read out from individual image zones of the sensor unit 11 and produce heat. The amplifier units 13 are arranged in such a manner that they adjoin the cooling unit 14 and hence a continuous reduction of the temperature can take place, so that all amplifier units 13 can operate at the same low temperature level. This enables all image zones of the sensor unit 11 to be amplified under the same conditions, thus avoiding the formation of incorrect renditions of the overall image. The cooling unit 14 receives the cooling medium of a constant temperature of 20° C. via the first duct sub-system 7 which is not shown in FIG. 3. The cooling medium is transported away from the X-ray detector 1 via a second sub-duct 8 (not shown either). A further processing unit 16 serves for the further processing of the amplified image signals and for the supply to peripheral apparatus.

We claim:

1. An X-ray examination apparatus comprising:
   a supporting device (3) for supporting an X-ray detector (1) and an X-ray source (2), and
   a system of ducts (7, 8, 9) which is coupled to a heat exchanger (6), the X-ray detector (1) and the X-ray source (2) forming a closed loop system, the system of ducts (7, 8, 9) circulating a cooling medium within the closed loop system for successively cooling the X-ray detector (1) and the X-ray source (2) before the cooling medium is applied to the heat exchanger (6).

2. An X-ray examination apparatus as claimed in claim 1, characterized in that the cooling medium is arranged to be applied, via a first duct sub-system (7), to the X-ray detector (1) in order to keep the temperature constant and, after a first exchange of heat between the cooling medium and the X-ray detector (1), to the X-ray source (2), via a second duct sub-system (8), and to the heat exchanger (6) via a third duct sub-system (9).

3. An X-ray examination apparatus as claimed in claim 1, characterized in that the X-ray detector (1) includes image point sensors which are arranged in the form of a matrix, groups of image point sensors being associated with amplifier units (13) for amplifying image signals.

4. An X-ray examination apparatus as claimed in claim 1, characterized in that the cooling medium is applied to the X-ray detector at a constant temperature.

5. An X-ray examination apparatus as claimed in claim 1, characterized in that, after a first exchange of heat with the X-ray detector, the cooling medium can be applied to the X-ray source without temperature reduction or cooling.

6. An X-ray examination apparatus as claimed in claim 1, characterized in that the X-ray detector is provided with a temperature sensor (17) for producing a signal (15) that is dependent on temperature, the temperature signal (15) being applied to the heat exchanger (6) in order to control the temperature of the cooling medium.

7. An X-ray examination apparatus as claimed in claim 1, characterized in that the heat exchanger (6) is arranged outside the supporting device (3).

8. An X-ray detector comprising a sensor unit (11) which converts the X-rays into electrical signals, a processing unit (12) which adjoins the sensor unit (11) and includes a plurality of amplifier units (13) that are associated with a cooling unit (14) which contains a cooling medium that enables the temperature of all amplifier units (13) to be kept constant as well as the cooling of the X-ray converter unit (11a) provided in the sensor unit (11), wherein the cooling unit is in fluid communication with a duct system (7, 8, 9) forming a closed loop system for circulating the cooling medium within the closed loop system for successively cooling the cooling unit (14) of the X-ray detector and an X-ray source (2) before the cooling medium is applied to a heat exchanger (6).

9. A method of cooling X-ray examination apparatus, comprising the steps of:
   providing a system of ducts (7, 8, 9) forming a closed loop system;
   circulating a cooling medium within the closed loop system for successively cooling an X-ray detector (1) and an X-ray source (2); and
   applying the cooling medium to a heat exchanger (6) following cooling of the X-ray source (2).

* * * * *